United States Patent [19]

Zimmermann et al.

[11] Patent Number: 4,822,616
[45] Date of Patent: Apr. 18, 1989

[54] VAGINAL RING

[75] Inventors: Ingfried Zimmermann; Fred Windt; Hans-Jürgen Reck, all of Berlin, Fed. Rep. of Germany

[73] Assignee: Schering Aktiengesellschaft, Berlin and Bergkamen, Fed. Rep. of Germany

[21] Appl. No.: 14,316

[22] Filed: Feb. 13, 1987

Related U.S. Application Data

[63] Continuation of Ser. No. 316,011, Oct. 28, 1981, abandoned.

[30] Foreign Application Priority Data

Oct. 28, 1980 [DE] Fed. Rep. of Germany ....... 3040978

[51] Int. Cl.$^4$ .............................................. A61M 7/00
[52] U.S. Cl. ................................ 424/432; 604/891.1; 424/430
[58] Field of Search ............... 424/432, 424/430–433, 424/422, 424; 604/890, 891

[56] References Cited

U.S. PATENT DOCUMENTS

| 4,012,496 | 3/1977 | Schopflin et al. | 424/15 |
| 4,012,497 | 3/1977 | Schopflin | 425/15 X |
| 4,155,991 | 5/1979 | Schopflin et al. | 424/15 |
| 4,292,965 | 10/1981 | Nash et al. | 128/127 X |

Primary Examiner—Nancy A. B. Swisher
Attorney, Agent, or Firm—Millen & White

[57] ABSTRACT

A vaginal ring comprises a supporting ring 1 free of active agent. A layer 2, which contains an active agent such as a steroid, is applied on its outer rim, optionally in a continuous groove provided in the supporting ring. This layer, in turn, is coated with a layer 3 devoid of active ingredient. All components preferably comprise an LTV silicone elastomer. The ratio of the thickness of the layer 2, containing an active agent, to the layer 3, free of active agent, is about 5–50:1. As a result, a long-term and uniform release rate is achieved for the active agent.

13 Claims, 2 Drawing Sheets

VAGINAL RING

CROSS-REFERENCE TO RELATED APPLICATIONS

This application is a continuation of U.S. Ser. No. 316,011, filed 10/28/81, now abandoned.

This application is related to commonly assigned U.S. Pat. No. 4,012,496 and to U.S. application Ser. No. 202,823, filed on Oct. 31, 1980, which is a continuation of U.S. application Ser. No. 785,792, filed on Apr. 8, 1977, the disclosures of all being incorporated by reference herein.

BACKGROUND OF THE INVENTION

The present invention relates to vaginal rings.

Vaginal rings composed of synthetic resins, and containing active ingredients, have been known for some time. DOS No. 2,450,107 and its U.S. equivalent 4,012,496 describe a vaginal ring consisting of a supporting ring with one or two continuous pocket-like indentations adapted to accommodate active-agent-containing rings which fit into these indentations and are made of a synthetic LTV silicone elastomer resin.

U.S. Pat. No. 3,920,805 likewise describes a vaginal ring of a silicone elastomer consisting of a core free of active agent and a coating containing an active agent.

Both systems have in common that the active ingredient is released directly to the surrounding body parts from the part containing the active agent.

However, annular devices are likewise conventional wherein the part containing the active agent is coated with a diaphragm free of active ingredient (U.S. Pat. No. 3,854,480). In this device, the annular core consists of a silicone elastomer containing an active agent, encompassed by a polyethylene hose having a wall thickness of about 0.8 mm.

The conventional vaginal rings, however, are disadvantageous in that the release rate over the desired time period is not constant. Rather, the amount per unit time becomes increasingly smaller after an initial surge of active agent.

SUMMARY OF THE INVENTION

Accordingly, it is an object of the present invention to provide a vaginal ring having a release of active agent which is of uniform regularity and of long duration.

Upon further study of the specification and appended claims, further objects and advantages of this invention will become apparent to those skilled in the art.

These objects have been attained by providing a vaginal ring comprising a supporting ring 1 free of active agent; a layer 2 applied to its outer rim and containing an active steroid agent, there being no medicament-containing layer on the inner rim; a layer 3 devoid of active agent coated onto layer 2; wherein the ratio of the thicknesses of the layer 2, containing an active agent, and the layer 3, free of active agent, is about 5-50:1. The supporting ring 1 can have a continuous groove to accommodate the layer 2.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein:

FIG. I schematically illustrates a top view of a vaginal ring of this invention;

FIGS. II and III show a section A-B of two embodiments of such a ring; and

FIG. IV shows the uniformity of release of active agent from a vaginal ring of this invention. (Release per day over a time period of more than 2 months.)

DETAILED DISCUSSION

The vaginal ring of this invention has an average outer dimension of 0.5-20 cm, the exact size being dependent on the particular application. In the case of relatively small mammals, such as dogs, the ring size will be smaller than in the case of relatively larger mammals, such as horses or cows. For Rhesus monkeys, for example, the outer diameter is about 2-3 cm. In vaginal rings for human females, the outer diameter is about 5-7 cm and the largest width of the ring cross section (See, e.g., Section A-B of FIGS. I to III) is 5-10 mm. Dimensional details for any ring for any application can be conventionally determined, if necessary, using routine preliminary experiments.

In a special embodiment of the supporting ring 1, a groove is contained in its outer rim for engaging layer 2. (See, e.g., FIG. III as well as other variants shown in U.S. Pat. No. 4,012,496.)

Unless indicated otherwise herein, all details of all aspects of this invention are fully conventional and can be determined by analogy to those of U.S. Pat. No. 4,012,496, and of U.S. application Ser. No. 202,823, which are incorporated by reference herein. Such details include but are not limited to chemical compositions of the layers, active drugs, overall sizes and shapes, cross-sectional sizes and shapes of the ring and individual ring components, methods of construction and preparation of each ring component, etc.

Figure 1:
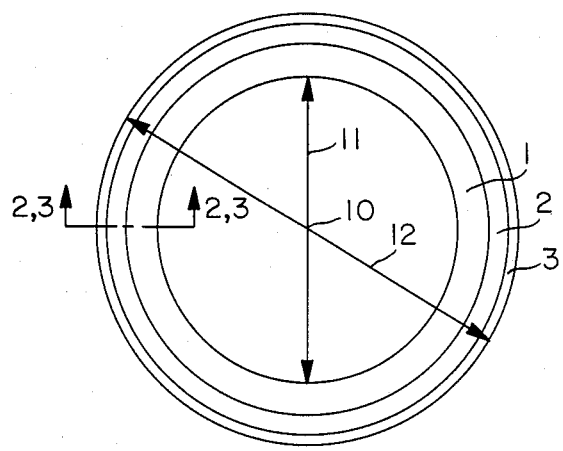
Figure 2:
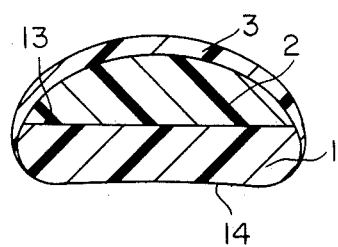
Figure 3:
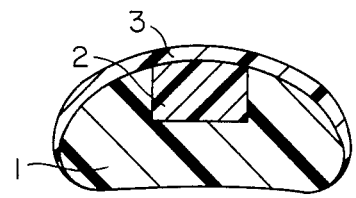

A special embodiment of the invention has an outer diameter of 58 to 60 mm, an inner diameter of 50 to 52 mm, and the largest width of the non-circular cross-section (see, e.g., section A-B of FIGS. 2 or 3) is 6.5 to 7.5.

The supporting ring 1 comprises a physiologically acceptable synthetic resin, such as, for example, polyethylene, RTV silicone elastomers, LTV silicone elastomers, polyamides, and polytetrafluoroethylene. An especially suitable synthetic resin is LTV silicone elastomer whose vulcanization behavior with respect to the layer 2 containing the active ingredient does not cause any technical problems.

A preferred LTV silicone elastomer has the following composition:

80–98% by weight of polydimethylvinylsiloxane

1–10% by weight of tetramethyltetravinylcyclotetrasiloxane

2–20% by weight of polydimethyl hydrogen siloxane 0.5–10% by weight of highly disperse silicic acid; and 10–100 ppm of platinum catalyst.

Suitable platinum catalysts include metallic platinum per se, platinum on support materials, such as silica gel, or platinum in the form of its salts, e.g., platinum carbonyl dichloride or platinum dicarbonyl dichloride, or as hexachloroplatinic acid. Also suitable are platinum complexes of unsaturated siloxanes (cf. U.S. Pat. No. 4,166,078 whose disclosure is incorporated by reference herein).

The Composition for producing the supporting ring can optionally also contain, in addition to highly dispersed silicic acid, which influences primarily only the mechanical properties, also other auxiliary materials, such as, for example, tensides, solubilizers, coloring agents, etc., as long as they are inert with respect to the total system.

The layer 2 containing the active agent comprises as a base composition, a pharmaceutically acceptable resin from which the agent can be released, e.g., as described in U.S. Pat. No. 4,012,496. Especially preferred is a combination of drug and LTV silicone elastomer, particularly one of the following composition:

75-98% by weight of polydimethylvinylsiloxane
1-10% by weight of tetramethyltetravinylcyclotetrasiloxane
1-10% by weight of polydimethyl hydrogen siloxane
10-100 ppm of a platinum catalyst, and
1-10% by weight of active agent.

Suitable active agents are any of those for which administration is possible by a vaginal ring and which are compatible with the system and methodology of this invention. Especially suitable as active agents are those which are nonionic and lipid-soluble, especially steroid hormones having a progestational or estrogenic activity. Examples in this connection are ethynylestradiol, ethisterone, norethisterone acetate, norethynodrel, levonorgestrel, or gestodene.

The layer 3, free of active agent, likewise can comprise any LTV silicone elastomer.

Especially preferred is an LTV silicone elastomer, particularly one having the following composition:

75-98% by weight of polydimethylvinylsiloxane
1-10% by weight of tetramethyltetravinylcyclotetrasiloxane
2-20% by weight of polydimethyl hydrogen siloxane, and
10-100 ppm of a platinum catalyst.

The devices of this invention are manufactured according to fully conventional methods such as, preferably, by the injection molding technique for layers 1 and 2. Specific details for forming any component or overall device of this invention or for forming any composition are fully conventional and can be determined readily from U.S. Pat. No. 4,012,496, for example. All starting materials are known.

For example, the amount of polydimethylvinylsiloxane employed is advantageously first divided typically into portions of 1 to 1. One portion is used together with the polydimethyl hydrogen siloxane, and the other together with the platinum catalyst. The two portions are combined only shortly before vulcanization and are crosslinked by temperature increase.

The active agent is suitably micronized before being incorporated into the liquid mixture of the starting components.

The layer 3, free of active ingredient, is likewise applied according to methods known per se, such as dipping or spraying using fully conventional procedures for such techniques. The layer thickness is generally 10-1,000 preferably 100-500 $\mu$m. The ratio of thickness of layer 2 to layer 3 is 5-50:1, preferably 20-40:1.

The vaginal ring of this invention has the advantage that the active agent is released over a relatively long period of time within the limits of the dosage required for the biological effect desired, e.g., the dose necessary for inhibition of ovulation, in a regular and uniform fashion.

Considering the structure of the vaginal ring in more detail, the ring is defined about an axis of revolution 10 and has an inner diameter 11 and an outer diameter 12. The vaginal ring has a radial thickness in the direction of the axis. As is seen in FIGS. II and III, the supporting ring 1 has a first surface 13 on which the first annular layer 2 of pharmacologically acceptable material is placed and an exposed surface 14 which in use faces the uterus. The second annular 3 pharmacological layer 3 completely overlies the first layer 2 and is in direct contact with the supporting layer 1.

The use of the vaginal rings of this invention is fully conventional including methods and precautions of insertion, maintenance and removal, except, of course that advantage can be taken of the long-term and regular drug release provided.

Without further elaboration, it is believed that one skilled in the art can, using the preceding description, utilize the present invention to its fullest extent. The following preferred specific embodiments are, therefore, to be construed as merley illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

The following components are thoroughly mixed for producing the supporting ring 1

232.577 g of vinyl-terminated polydimethylsiloxane having an average molecular weight of $\overline{M}$ 5854,
17.423 g of tetramethyltetravinylcyclotetrasiloxane and
25.000 mg of platinum (mixture A1), as well as
193.789 g of vinyl-terminated polydimethylsiloxane and
56.211 g of polydimethyl hydrogen siloxane (mixture B1).

The two mixtures A1 and B1 are homogenized in a static mixing pipe, introduced into an injection molding tool, and vulcanized during a period of 60 seconds at 100° C. into rings having a cross section of a circular segment.

The Shore A hardness is 45, and the elongation at rupture is 50%.

To produce the layer 2, containing the active agent, the following componentsare mixed intensively 49.86 g of vinyl-terminated polydimethylsiloxane ($\overline{M}$=8170),
0.14 g of tetramethyltetravinylcyclotetrasiloxane,
5.00 mg of platinum, and
1.814 g of levonorgestrel (mixture A2), as well as
48.61 g of vinyl-terminated polydimethylsiloxane ($\overline{M}$=8170),
1.39 g of polydimethyl hydrogen siloxane, and
1.814 g of levonorgestrel (mixture B2).

The two mixtures A2 and B2 are homogenized in a static mixing pipe, introduced into an injection molding tool with inserted supporting rings 1, and vulcanized onto the outer rim of the supporting ring 1 for a period of 60 seconds at 100° C.

The thus-produced vaginal rings are sprayed, in the region of the layer 2 containing the active agent, with a layer 3 of silicone elastomer having a thickness of about 200 $\mu$m. This layer forms a composite vulcanizate with the layer 2 disposed therebelow.

The silicone elastomer mixture for the layer 3 free of active ingredient is composed of

- 42.53 g of vinyl-terminated polydimethylsiloxane ($\bar{M}$=4561),
- 5.72 g of polydimethyl hydrogen siloxane,
- 1.75 g of tetramethyltetravinylcyclotetrasiloxane, and
- 50 ppm of platinum.

The individual ring contains accordingly 0.8% of active ingredient and has a release rate of 70.5 μg/d.

EXAMPLE 2

Analogously to Example 1, supporting rings 1 are produced from

- 233.98 g of vinyl-terminated polydimethylsiloxane ($\bar{M}$=8170),
- 16.02 g of tetramethyltetravinylcyclotetrasiloxane,
- 25.00 mg of platinum, and
- 13.158 g of highly disperse silicic acid, as well as
- 203.92 g of vinyl-terminated polydimethylsiloxane ($\bar{M}$=8170),
- 46.08 g of polydimethyl hydrogen siloxane, and
- 13.158 g of highly disperse silicic acid.

The Shore A hardness is 65, and the elongation at rupture is 75%.

A layer 2 containing active ingredient is vulcanized onto the supporting rings 1, this layer having the following composition:

- 239.38 g of vinyl-terminated polydimethylsiloxane ($\bar{M}$=8170),
- 10.62 g of tetramethyltetravinylcyclotetrasiloxane,
- 25.00 mg of platinum catalyst,
- 27.778 g of levonorgestrel, as well as
- 217.70 g of vinyl-terminated polydimethylsiloxane ($\bar{M}$=8170),
- 32.30 g of polydimethyl hydrogen siloxane,
- 27.778 g of levonorgestrel.

Thereafter a layer 3 free of active agent and having a thickness of 350 μm is applied to the layer 2 containing the active ingredient, this layer 3 having the following composition:

- 47.061 g of vinyl-terminated polydimethylsiloxane ($\bar{M}$=8170),
- 0.681 g of tetramethyltetravinylcycltetrasiloxane,
- 2.258 g of polydimethyl hydrogen siloxane, and
- 50 ppm of platinum.

The individual ring contains accordingly 2.3% by weight of active agent and has a release rate of 45 μg/d.

EXAMPLE 3

The same blend as set forth in Example 1 is used for producing the supporting ring 1, consisting of polydimethylsiloxane, tetramethyltetravinylcyclotetrasiloxane, platinum, as well as polydimethyl hydrogen siloxane.

The two mixtures A1 and B1 are homogenized in a static mixing pipe, introduced into an injection molding tool, and vulcanized for a period of 60 seconds at 100° C. into rings having a continuous groove, as shown in FIG. III.

Subsequently, a composition containing an active ingredient, consisting of the two mixtures A2 and B2, Example 1, is injected into the groove and vulcanized for 60 seconds at 100° C. Thereafter, the layer 3, free of active ingredient and having the same composition as in Example 1, is applied to the thus-manufactured ring.

The individual ring has an active agent release rate of 20 μg/d.

EXAMPLE 4

Figure 4:
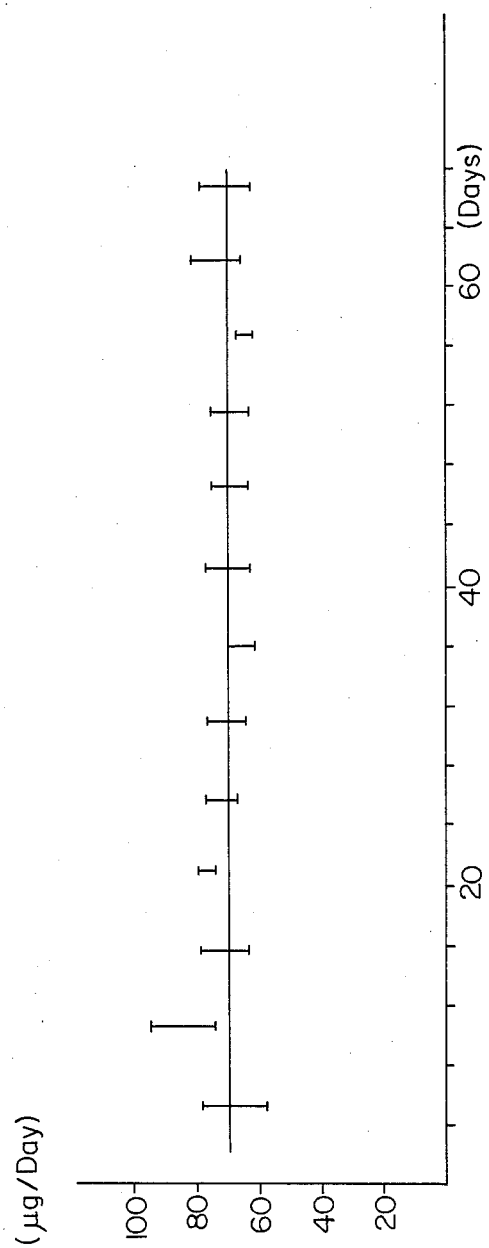

The in vitro release rates (See FIG. 4) are measured as follows: The ring is fit to a support and placed in vessels containing 200 ml of double-destilled water. The ring is fixed about 10 mm above the bottom of the vessel which has a diameter of 85 mm and a height of 90 mm. After an incubation period of 24 hours at 37° C. the levonorgestrel containing water is exchanged and analysed. The levonorgestrel dissolved in the water is concentrated by means of a chromatographic column filled with lipophilized silica gel. By pressing the water through the column, the steroid is bound by the aliphatic residues to the surface of the silica gel. The bound steroid is then removed by elution of the column with 5 ml of methanol. The concentration of steroid is determined spectrophotometrically at a wavelength of 248 nm.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A vaginal ring spaced from an axis of revolution, the ring having an inside diameter and an outside diameter, a radial thickness with respect to the axis and an axial thickness in the direction of the axis, the ring having first and second exposed radial surfaces and the ring further comprising:

a supporting ring made of a pharmacologically acceptable material and being essentially free of medicament;

the supporting ring having a first annular surface between inner and outer circumferential peripheries extending in a radial direction and generally facing in a first axial direction, the supporting ring having a second annular surface extending in a radial direction with respect to the axis and facing in an axial direction opposite that of the first annular surface, the second annular surface being completely exposed;

a first annular layer made of a pharmacologically acceptable material and containing a pharmacologically active agent, the first annular layer extending in the axial direction and overlying radially the first annular surface of the supporting ring between the inner and outer circumferential peripheries thereof; and a second pharmacologically acceptable layer overlying the first annular layer in the axial direction; said second layer being essentially medicament free and being permeable to the active agent in the first layer; said second layer being thinner than the first layer in a ratio of 5-50:1, and also being in contact with the supporting layer at the inner and outer circumferential peripheries of the supporting layer, the second pharmacologically acceptable layer controlling the rate of migration of the activation from the first layer into the vagina.

2. The vaginal ring of claim 1, wherein the first surface of the supporting includes a groove therein inboard of the inner and outer circumferential peripheries in which the first layer containing the pharmacologically active ingredient is inserted.

3. A vaginal ring of claim 1, wherein the thickness of the second layer is 10–1000 μm.

4. A vaginal ring of claim 1, wherein the thickness of the second layer is 100–500 μm.

5. A vaginal ring of claim 3, wherein each of said two layers comprises an LTV silicone elastomer.

6. A vaginal ring of claim 5, wherein the second layer consists essentially of an LTV silicone elastomer of the following composition:
   75–98% by weight of polydimethylvinylsiloxane
   1–10% by weight of tetramethyltetravinylcyclotetrasiloxane
   2–20% by weight of polydimethyl hydrogen siloxane, and
   10–100 ppm of platinum catalyst.

7. A vaginal ring of claim 6, wherein the supporting ring consists essentially of an LTV silicone elastomer of the following composition:
   80–98% by weight of polydimethylvinylsiloxane
   1–10% by weight of tetramethyltetravinylcyclotetrasiloxane
   2–20% by weight of polydimethyl hydrogen siloxane
   0.5–10% by weight of highly disperse silicic acid, and
   10–100 ppm of a platinum catalyst and the first layer consists essentially of an active agent and an LTV silicone elastomer and has the following composition:
   75–98% by weight of polydimethylvinylsiloxane
   1–10% by weight of tetramethyltetravinylcyclotetrasiloxane
   1–10% by weight of polydimethyl hydrogen siloxane
   10–100 ppm of a platinum catalyst, and
   1–10% by weight of active agent.

8. A vaginal ring of claim 1, wherein the active agent in the first layer is a steroidal progestogen, a steroidal estrogen or a combination thereof.

9. A vaginal ring of claim 8, wherein the active agent is ethynylestradiol, ethisterone, norethisterone acetate, norethynodrel, levonorgestrel, or gestoden or a mixture thereof.

10. A method of vaginally administering a pharmacologically active agent to a host in need of such administration which comprises inserting a vaginal ring of claim 1, into the vagina of the host.

11. A method of claim 10, for inhibiting ovulation in a host wherein the active agent in the vaginal ring is effective to inhibit ovulation.

12. A vaginal ring of claim, wherein the ratio of the thickness of the first layer to that of the second layer is about 20–40:1.

13. A vaginal ring of claim 1, wherein each of said two layers comprises an LTV silicone elastomer.

* * * * *